US009125734B2

(12) United States Patent
Keller et al.

(10) Patent No.: US 9,125,734 B2
(45) Date of Patent: Sep. 8, 2015

(54) ARTIFICIAL RETINA THAT INCLUDES A PHOTOVOLTAIC MATERIAL LAYER INCLUDING A TITANIUM DIOXIDE SEMICONDUCTOR

(75) Inventors: Nicolas Keller, Holtzheim (FR); Pierre Bernhardt, Heiligenberg (FR); Michel Roux, Strasbourg (FR); Anne Robe, Illkirch-Graffenstaden (FR); Shankar Muthukonda Venkatakrishnan, Andra Pradesh (IN); Serge Picaud, Avon (FR); Marc J. Ledoux, Neoules (FR); Valerie Keller-Spitzer, Oberschaeffolsheim (FR); Thomas Cottineau, Strasbourg (FR)

(73) Assignees: CENTRE NATIONAL DE LA RECHERCHE SCIENTIFIQUE (C.N.R.S.), Paris (FR); UNIVERSITE DE STRASBOURG, Strasbourg (FR)

( * ) Notice: Subject to any disclaimer, the term of this patent is extended or adjusted under 35 U.S.C. 154(b) by 65 days.

(21) Appl. No.: 13/514,587

(22) PCT Filed: Dec. 7, 2010

(86) PCT No.: PCT/FR2010/052633
§ 371 (c)(1),
(2), (4) Date: Sep. 11, 2012

(87) PCT Pub. No.: WO2011/070288
PCT Pub. Date: Jun. 16, 2011

(65) Prior Publication Data
US 2013/0023986 A1    Jan. 24, 2013

(30) Foreign Application Priority Data

Dec. 8, 2009    (FR) .................................... 09 58744

(51) Int. Cl.
| A61F 9/08 | (2006.01) |
| A61N 1/05 | (2006.01) |
| A61N 1/36 | (2006.01) |
| A61F 9/007 | (2006.01) |

(52) U.S. Cl.
CPC ................ *A61F 9/08* (2013.01); *A61N 1/0543* (2013.01); *A61N 1/36046* (2013.01); *A61F 9/00727* (2013.01); *Y02E 10/52* (2013.01)

(58) Field of Classification Search
CPC .... A61N 1/36046; A61N 1/0543; A61F 9/08; A61F 2/14; A61F 2/141; A61L 2400/12
USPC ................................................ 623/6.56, 6.63
See application file for complete search history.

(56) References Cited

U.S. PATENT DOCUMENTS 6,298,270 B1    10/2001  Nisch et al.
7,153,808 B2 *  12/2006  Iwamoto et al. .............. 502/200
(Continued)

FOREIGN PATENT DOCUMENTS

WO    WO 02/102241 A2    12/2002
WO    WO 2004/071338 A2   8/2004

OTHER PUBLICATIONS

Tokudome et al., N-doped TiO2 Nanotube with Visible Light Activity, Chemistry Letters vol. 33, No. 9, pp. 1108-1109.*

*Primary Examiner* — Howie Matthews
(74) *Attorney, Agent, or Firm* — Knobbe, Martens, Olson & Bear, LLP

(57) ABSTRACT

An artificial retina that includes: (i) a substrate; (ii) a first layer, placed onto said substrate and including photovoltaic material portions separated by at least one insulating material portion; and (iii) a second layer, placed onto said first layer and including conductive material portions separated by at least one insulating material portion. In said artificial retina, the photovoltaic material includes a titanium dioxide semiconductor.

15 Claims, 8 Drawing Sheets

(56) References Cited

U.S. PATENT DOCUMENTS

| | | | |
|---|---|---|---|
| 8,241,917 B2 * | 8/2012 | Fan et al. | 436/145 |
| 8,588,920 B2 * | 11/2013 | Naughton | 607/54 |
| 2002/0111655 A1 * | 8/2002 | Scribner | 607/54 |
| 2007/0005116 A1 | 1/2007 | Lo | |
| 2011/0270153 A1 * | 11/2011 | Olson | 604/20 |

* cited by examiner

ARTIFICIAL RETINA THAT INCLUDES A PHOTOVOLTAIC MATERIAL LAYER INCLUDING A TITANIUM DIOXIDE SEMICONDUCTOR

The present invention relates to artificial retinas or retinal prostheses.

The retina is formed of an array of photoreceptors which capture light signals and convert them to electric pulses transmitted to the retinal network of internal neurons which then convey the same to the optical nerve via the brain's visual centers.

The objective of an artificial retina is to restore useful vision in blind patients suffering from degeneration of the photoreceptors due to retinitis pigmentosa for example or to age-related macular degeneration (accounting for more than 50% of blind conditions in France). When the photoreceptors degenerate, the network of internal neurons subsists in part. An artificial retina then allows images to be captured and converts them to electric signals capable of stimulating these neurons so as to restore sufficient vision to allow locomotion, face recognition, reading . . . .

Different artificial retinas have been developed.

One technique uses a camera which sends electric signals to a receiver also ensuring energy supply that is installed on the periphery of the eye, itself connected via cable to an artificial retina in the form of an array of metal electrodes (16 to 60 electrodes) placed in contact with the retina, in contact with the surviving neurons (Artificial Retina News, Autumn 2006, Winter 2007, Summer 2009). The materials used for these electrodes are platinum or iridium oxide in particular. However, this technique comes up against the problem of miniaturizing the electronic circuits. Current models have 60 electrodes and the limit of 1000 electrodes, considered to be the minimum to hope for face recognition, will no doubt not be reached before several years.

An alternative technique consists of implanting photodiodes in contact with the retina which comprise silicon-based photosensitive materials (Besch et al., Br. J. Ophthalmol. 2008, 92(10): 1361-8). However, current photodiodes require high light levels to emit sufficient current to prompt neuron response. The yield of current photodiodes therefore requires amplification of the current produced. This approach is used by the company Retinal Implant AG®. The reported results are highly encouraging. However, it is supplied by a cable starting at the intraocular element and passing under the skin to emerge at the back of the head. This cable provides energy supply and allows control of the amplifiers. Said apparatus, at least at the current time, therefore entails the continued existence of a cable through the ocular wall, and strong limitation even the absence of eye movements. The patient's eye is immobilized. Yet, since an image projected non-variant fashion onto the retina is no longer perceived, the retina and the human brain are not used to working with fixed images but on the contrary use variations in time. The loss of eye mobility can only partly be offset by head movements, since these movements cannot take place at the same frequency as saccadic eye movement. In addition, the presence of a cable also involves the increased risk of endophthalmitis (intraocular infection) or hypotonus (lowered intraocular pressure).

Another technique is based on a prosthesis consisting of infrared-sensitive, silicon-based photodiodes (Daniel Palanker group, University of Stanford). The advantage is that for a given energy level, infrared is less harmful than visible light. However, the models developed include an amplification system drawing energy from part of infrared light. This prosthesis must additionally comprise glasses converting visible light to infrared light.

Also, it has been proposed to use films of semiconductor nanoparticles in HgTe (Pappas et al., Nanoletters, 7(2), 513-519, 2007) and PbSe (Zhao et al., Angew. Chem. Int. Ed. Engl. 48, 2407-2410, 2009), for electric stimulation of the neurons. However, these semiconductors are toxic for the body and their implanting in the body therefore gives rise to problems.

It is the objective of the invention to propose an artificial retina allowing the afore-mentioned disadvantages to be overcome, in particular an artificial retina not requiring the continued use of a cable passing through the ocular wall.

For this purpose, according to a first aspect, the invention concerns an artificial retina comprising:
 (i) a substrate;
 (ii) a first layer placed onto said substrate and comprising photovoltaic material portions separated by at least one insulating material portion;
 (iii) a second layer placed onto said first layer and comprising conductive material portions separated by at least one insulating material portion,
wherein the photovoltaic material comprises a titanium-based semiconductor.

Indeed, the use of a titanium-based semiconductor allows an artificial retina to be obtained having high yields. The artificial retina of the invention is therefore able to emit a sufficient signal whilst being biocompatible and hence implantable in the individual's body.

The retina is a thin nerve structure located at the back of the eye covering about 75% of the eyeball (FIGS. 1 and 2). It ensures the sensitive part of vision converting the light image focused by the eye lenses (cornea and crystalline lens) to an electric signal transmitted to the upper vision centers via the optical nerve in the form of action potentials. An artificial retina is a device capable of converting light to electricity intended to stimulate some non-photosensitive retinal neurons which may have survived despite the loss of natural photoreceptors.

An artificial retina can be implanted either in contact with the ganglion cells or at the position of the retinal photoreceptors. The terms epiretinal mode or sub-retinal mode are respectively used.

The artificial retina of the invention will preferably be used in sub-retinal mode (FIG. 2) so as to make use of the entire subsisting retinal network after loss of the photoreceptors.

Advantageously, the artificial retina of the invention does not require any external energy supply to the implanted element, other than in the form of light, this light typically being at wavelengths of the visible spectrum and/or those of the near infrared. Therefore, it does not need to be connected to external devices in order to function: the artificial retina is therefore generally a wireless retina. The eyes in which the retina is grafted are left free to move.

Preferably, a point-to-point projection system or glasses of virtual reality type are associated with the artificial retina. The point-to-point projection system or glasses ensure amplification of the image in low light and on the contrary attenuation under strong light, and facilitate functioning of the artificial retina over a luminosity range compatible with independent mobility of the individual in whom the retina is implanted. No cable is needed between the artificial retina and the point-to-point projection system or the glasses.

Preferably, the thickness of the artificial retina is between 5 and 250 μm, in particular between 10 and 100 μm, and its length and width is between 2×2 mm and 10×10 mm, in particular between 3×3 mm and 5×5 mm. These sizes are adapted for implanting the retina at the macula (central portion of the retina used for high resolution vision, which measures about 2 mm in diameter).

The artificial retina may be planar, in particular for retinas having a length and width of the order of 2×2 mm or 3×3 mm, with a circular or elliptical shape for example. It may also have a curved shape compatible with the curvature of the eye, e.g. an elliptic paraboloid. This curved shape is adapted for larger retinas having a length and width of the order of 5×5 mm for example.

The substrate therefore acts as support for the first layer and second layer of the artificial retina.

The substrate may be opaque. For example, substrates in polyimide are suited. An opaque substrate prevents the passing of light as far as the eye fundus, which limits reflections inside the eyeball and therefore avoids possible image degradation. However, the substrate may also be transparent. A substrate in diamond for example may be used. Diamond combines the advantages of strong mechanical strength, good electric insulation and biocompatibility. A substrate comprising several materials may be used, for example a substrate comprising a layer of diamond imparting the afore-mentioned advantages and a polyimide layer to opacify the substrate.

The first layer of the artificial retina comprises portions in photovoltaic material separated by at least one portion in insulating material. By <<portions in photovoltaic material>> is meant portions comprising or consisting of a photovoltaic material, and by <<portion in insulating material>> is meant a portion comprising or consisting of an insulating material.

The photovoltaic material allows conversion of incident light to electricity.

The photovoltaic material of the artificial retina according to the invention comprises a titanium-based semiconductor. In general, the photovoltaic material of the artificial retina comprises at least 50% of titanium-based semiconductor, typically at least 75% and in particular at least 85%, preferably at least 90%.

A semiconductor is a material which has intermediate electric conductivity between that of a conductive material and that of an insulating material, namely in general within the range of $10^{-5}$ Ω.m (ohm.metre) to $10^{2}$ Ω.m. The behavior of semiconductors, like the behavior of metals and insulators is described using the theory of band structure which stipulates that an electron in a solid is confined to energy values lying within certain intervals called allowed bands, which are separated by other bands called forbidden bands. When the temperature of the solid tends towards absolute zero, two allowed energy bands play a particular role: the last completely filled band called <<valence band>> and the following allowed energy band called <<conduction band>>. The valence band is rich in electrons but does not take part in conduction phenomena (for the electrons). The conduction band however is either empty of electrons (as at temperatures closed to absolute zero in a semiconductor) or half-filled with electrons (as is the case for metals). However, it is this band which enables the electrons to circulate within the solid. In a semiconductor, as in an insulator, these two bands are separated by a forbidden band commonly called a <<band gap>>. The only difference between a semiconductor and an insulator is the width of this band gap, a width which gives each one its respective properties. In an insulator the value of the band gap is so high (in the region of 6 eV for diamond for example) that the electrons are unable to pass from the valence band to the conduction band: the electrons do not circulate in the solid. In semiconductors, this value is smaller, generally of the order of 0.5 to 3.5 eV (1.12 eV for silicon, 0.66 eV for germanium, 2.26 eV for gallium phosphide, 3.2 eV for titanium dioxide (anatase)). If this energy (or higher) is imparted to the electrons, for example by heating the material, or by applying an electromagnetic field thereto, or even by illumination, the electrons are then capable of passing from the valence band to the conduction band and to circulate in the semiconductor material whilst leaving a non-occupied energy state in the valence band called a <<hole>>.

Preferably, the titanium of the semiconductor is titanium dioxide ($TiO_2$), titanium oxyhydroxide ($H_2Ti_3O_7$), a metal titanate or a mixture of these compounds. A metal titanate is a titanate whose counter-ion is a metal cation, in particular an alkaline, alkaline-earth, transition metal or base metal titanate. Potassium or lithium titanate are examples of an alkaline titanate. Calcium or barium titanate are examples of an alkaline-earth titanate. Zirconium, zinc or iron titanate are examples of a transition metal titanate. Aluminium titanate is an example of a base metal titanate. By <<base metal>> is meant aluminium, gallium, indium, tin, thallium, lead and bismuth. Advantageously, the semiconductor is biocompatible, as are titanium oxyhydroxide and titanium dioxide. Titanium dioxide, titanium oxyhydroxide and the mixtures of titanium dioxide and titanium oxyhydroxide are particularly preferred titanium-based semiconductors.

The titanium-based semiconductor can be doped, in particular with the elements carbon, nitrogen, sulfur and/or tungsten which allows shifting of the absorption spectrum of the semiconductor, and hence of the artificial retina, towards one or other part of the spectrum, for example to benefit from better response to visible light. However, absorption of the semiconductor in visible light is not compulsory. Absorption in the infrared is less harmful for a given energy level. In addition for an individual in whom only part of the photoreceptors have been damaged, the other part of the photoreceptors still remaining functional, if the artificial retina absorbs in the infrared it is possible to combine the effects of infrared stimulation of the artificial retina with those of visible light stimulation of the photoreceptors still remaining functional. In order to reach optimum perception, the perceived image can be converted by an external camera to an optimized image for the resolution of the implanted artificial retina and encoded in the wavelengths the best absorbed by the titanium-based semiconductor used.

Titanium dioxide is the preferred titanium-based semiconductor on account of its low cost, photovoltaic yield and good biocompatibility.

The artificial retina of the invention is advantageously less costly to prepare than artificial retinas containing silicon photodiodes.

Titanium dioxide is advantageously biocompatible. Moreover titanium dioxide is used as food coloring (E171) and titanium is used in numerous types of prostheses (hip prostheses, stirrup for ear prostheses, jaw reconstruction, skull implants, orthodontic anchor points . . . ). This biocompatibility is a major advantage for use in an artificial retina to be implanted in a patient.

Titanium dioxide exists in different crystalline forms. Titanium dioxide can be in the form of rutile, anatase, brookite, srilankite, $TiO_2$ α or $TiO_2$ β. The light wavelengths able to activate titanium dioxide vary in relation to its crystalline form. For example titanium dioxide in anatase form is activated by the UV-A fraction of sunlight, whereas titanium dioxide in rutile form is activated by the UV-A fraction and by the start of the visible spectrum of sunlight. The choice of crystalline form of titanium dioxide is therefore related to the wavelength at which the artificial retina is to function.

The titanium-based semiconductor in the photovoltaic material may be in particle or nanotube form. These nanotubes are formed using methods known to persons skilled in the art, for example by hydrothermal treatment e.g. at between 130 and 150° C. of a titanium-based semiconductor solution in an aqueous base solution e.g. sodium hydroxide. For example, the procedures described in the publications by T. Kasuga, M. Hiramatsu, A. Hoson, T. Sekino, K. Niihara, Langmuir 1998 (14) 3160—T. Kasuga, M. Hiramatsu, A. Hoson, T. Sekino, K. Niihara, Advanced Materials 1999 (11) 1307, or D. V. Bavykin, J. M. Friedrich, F. C. Walsh, Advanced Materials 2006 (18) 2807-2824 may be used. The structure of the nanotubes influences the physicochemical properties of the portion in photovoltaic material obtained, such as described for example in the article by T. Tachikawa, S. Tojo, M. Fujitsuka, T. Sekino, T. Majima, Journal of Physical Chemistry B 2006 (110) 14055. In the nanotubes, the phenomena of recombination of the photogenerated charges are limited owing to their displacement along the single-dimensional structure, which leads to improving the spatial separation of the charges of the portion in photovoltaic material. This increased separation leads to a longer lifetime of the electron-hole pairs and hence to a greater density of activated photogenerated charges in the semiconductor which may be transferred to the second layer, then to the neurons, thereby obtaining a higher yield of the artificial retina. In addition, by using nanotubes the pore size (inner cavity of the nanotube and spaces between the nanotubes) is larger than the size of the pores when particles are used (the pores then consisting of the spaces between the particles), the developed porosity is therefore more accessible, and therefore the diffusion of the liquid physiological medium that is present is advantageously benefited.

Preferably, the nanotubes used have an outer diameter of between 50 and 200 nm, typically of the order of 100 nm, and an inner diameter of 10 to 100 nm, typically of 20 nm to 90 nm. The length is strongly dependent on the duration of nanotube synthesis. Nanotube lengths of 1 to 50 µm, typically 3 to 30 µm are suitable for use as photovoltaic material in the retina.

In one embodiment, the titanium-based semiconductor in the photovoltaic material is in the form of nanotubes aligned with one another. Typically, the nanotubes are aligned relative to one another, the axes of the nanotubes being orthogonal to the plane of the substrate. By <<nanotubes aligned relative to one another and perpendicular to the plane of the substrate>>, is meant that at least 80%, even 95% of the nanotubes are contained in a cone of revolution of angle 10°, preferably 5° relative to the direction orthogonal to the substrate.

Indeed, the light flow passing through the aligned nanotubes is unidirectional, whereas the flow passing through particles or entangled nanotubes is multi-directional. A unidirectional light flow advantageously allows better light absorption to be obtained, since the loss through light scattering is smaller. The light flow enters over a depth (light penetration depth) in the nanotubes and allows the creation of photogenerated electrons. The photogenerated electrons also follow a rectilinear pathway along the aligned nanotubes rather than an erratic pathway from one particle to another inside a portion of photovoltaic material comprising a titanium-based semiconductor in the form of non-oriented particles, as illustrated in FIG. 14. This reduction in the pathway of the electrons means that the probability of electron recombination with the holes is advantageously reduced. Finally, nanotubes have much fewer grain boundaries (which also act as recombination centers) than particles and here again the probability of electron/hole recombination is reduced and the efficacy of the artificial retina is thereby improved. Also, the maximum resolution of the artificial retina is related to the minimum surface area of a pixel (cf. below) in order to generate sufficient current to depolarize the neuron(s) in contact with the retina. The alignment of the nanotubes minimizes the inter-nanotube space and promotes the penetration of the photons, compared with entangled nanotubes or with particles, thereby allowing pixels to be obtained that are both denser and thicker whose surface can therefore be reduced for one same stimulation efficacy i.e. increasing the resolution of the artificial retina of the invention.

The portions in photovoltaic material comprising the titanium-based semiconductor in the form of nanotubes aligned relative to one another are generally obtained by electrochemical anodizing followed by heat treatment, generally in a flow of air, at a temperature typically of between 400 and 600° C. and preferably for 1 to 12 hours, typically 2 to 4 hours.

Electrochemical anodizing is conducted using a potentiostatic system with two electrodes and by applying an anodic potential (positive) between titanium metal foil used as titanium precursor and platinum foil used as counter-electrode in a suitable electrolyte. For anodizing, the potential to be applied between the two electrodes is preferably between 20 and 100 V, in particular between 40 and 60 V, for efficient synthesis of the nanotubes. Anodizing generally lasts between 10 minutes and 100 hours, typically between 15 minutes and 2 hours.

If the substrate is titanium, electrochemical anodizing can be performed directly on the substrate. On the other hand, if the substrate is not in titanium (e.g. substrates in silicon, glass, transparent polymer material, etc. . . . ), a deposit step of titanium on the substrate is generally added prior to electrochemical anodizing, the metal titanium obtained on the surface of the substrate allowing the subsequent electrochemical anodizing step.

This depositing of titanium may advantageously be conducted by magnetron sputtering which consists of bombarding ions produced by argon plasma onto a target of metal titanium whose titanium atoms are ejected by the ions and come to be deposited on the substrate placed facing the target.

Different thicknesses of titanium deposited on the substrate can thus be obtained, typically between 100 nm and 3000 nm thick. Thicknesses of more than 500 nm are preferred to enable good formation of the nanotubes by electrochemical anodizing. Several parameters for magnetron sputtering allow the thickness of the deposit to be varied: sputtering time, plasma current intensity, temperature of the substrate and target-substrate distance depending on the apparatus used.

The portions in photovoltaic material comprising the titanium-based semiconductor in the form of nanotubes aligned relative to one another can be characterized by usual microscopy techniques, such as scanning electron and transmission microscopy, X-ray diffraction or UV-visible spectroscopy.

In one particular embodiment, the nanotubes aligned relative to one another are modified with a sensitizer i.e. a molecule or material allowing the absorption of photons of lesser energy than the band gap of the semiconductor, in $TiO_2$ in particular. This modification can be performed for example by chemically grafting the said sensitizer onto the nanotubes, using methods known to persons skilled in the art. The presence of the sensitizer allows increased light absorption in the visible range (wavelength>400 nm) by the portions in photovoltaic material, and hence by the retina. The sensitizer may in particular be:

a semiconductor having a band gap smaller than that of $TiO_2$, such as $WO_3$, CdS and CdSe, an organometallic coloring agent such as ruthenium polypyridine, an organic coloring agent e.g. boron-dipyrromethenes called Bodipy dyes.

In addition to or instead of modification with the above-mentioned sensitizer, the nanotubes aligned relative to one another may be doped with nitrogen, which allows increased light absorption in the visible range (wavelength>400 nm) by the portions in photovoltaic material, and hence by the retina. The preparation of nanotubes aligned relative to one another and doped with nitrogen can be also be performed by electrochemical anodizing, in particular by adding urea $N_2COH_4$ to the electrolyte, typically at between 0.1 and 0.5 mol.$L^{-1}$. The highest contents give the highest doping levels. The heat treatment following after anodizing can be conducted under the same conditions as mentioned above, except that the air flow is preferably replaced by a nitrogen flow.

In general, the widths and lengths of the portions in photovoltaic material are independent of each other and are between 10 μm and 300 μm, in particular between 20 μm and 200 μm. For a given retinal surface area, the greater the lengths/widths of the portions in photovoltaic material, the fewer the number of portions of photovoltaic material in the artificial retina (and hence the fewer the pixels as explained below), and the coarser the image reconstitution by the artificial retina. This is why the widths and lengths of the portions in conductive material are generally equal to or less than 200 μm.

The first layer of the artificial retina comprises portions of photovoltaic material separated by at least one portion in insulating material.

The insulating material of the first layer is an insulating material compatible with the substrate, the portions in photovoltaic material and the second layer, in particular through minimizing interface tension. An insulating material typically has resistivity of more than 1 Ω.m, typically $10^2$ Ω.m (ohm.metre), in particular $10^6$ Ω.m, preferably $10^{10}$ Ω.m to 300 K.

The insulating material may in particular be insulating diamond, a ceramic or an insulating polymer e.g. a polyimide or an epoxy resin, silicon or expanded polyethylene.

The thickness of the first layer is generally between 500 nm and 10 μm. The portions in insulating material and the portions in photovoltaic material of the first layer typically have the same thickness, which is the thickness of the first layer.

In the portions in photovoltaic material, when the titanium-based semiconductor is activated by light, positive charges are generated. These positive photogenerated charges, generally called <<holes>>, are positioned energy-wise in the valence band of the semiconductor material. More specifically, a semiconductor has a band gap electronic structure. When it is subjected to photon radiation of energy at least equal to that of the band gap, an electron is able to pass from the valence band to the conduction band. This gives rise to the creation of a hole in the valence band. These positive charges have strong oxidizing power and may degrade the neurons when in contact.

Therefore, the artificial retina of the invention also comprises a second layer comprising portions in conductive material separated by at least one portion in insulating material. By <<portions in conductive material>> is meant a portion comprising or consisting of a conductive material A conductive material is a material of low resistance whose resistivity is typically lower than $10^{-5}$ Ω.m (ohm.metre), particularly $10^{-6}$ Ω.m, preferably $10^{-7}$ Ω.m, at 300 K, which allows the current to be conveyed from one point to another.

At the interface between the portions in conductive material of the second layer and the portions in photovoltaic material of the first layer, the interface between the titanium-based semiconductor and the conductive material acts as Schottky barrier and prevents the transfer of positive charges to the neurons in contact with the artificial retina. A Schottky barrier is the potential barrier (i.e. the potential difference) formed at the interface between a conductor and a semiconductor. The height of this barrier reflects the difference between the energy position of the limit of the conduction band and the Fermi level of the conductor. The second layer of the artificial retina therefore allows the avoiding of degradation of the neurons by the positive charges.

The thickness of the second layer is generally 0.5 to 20 nm, particularly 1 to 10 nm, preferably 2 to 5 nm.

The conductive material is a conductive material compatible with the first layer which in particular allows interface tensions to be minimized between the first and second layers.

The conductive material may be a metal e.g. gold or platinum. The conductive material may also be titanium nitride or iridium oxide. Preferably, the conductive material is gold. The conductive material may also be conductive diamond (doped diamond) which advantageously has better mechanical strength than gold and excellent biocompatibility. The conductive material may also be a conductive polymer e.g. parylene-C(poly-dichloro-diparaxylylene).

In one embodiment, the thickness of the portions in conductive material is equal to the thickness of the portions in insulating material. In another embodiment, the thickness of the portions in insulating material is greater than the thickness of the portions in conductive material and the portions in insulating material project over the second layer. In another embodiment, the thickness of the portions in conductive material is greater than the thickness of the portions in insulating material and the portions in conductive material project over the second layer, in particular by 3 to 50 μm, for example from 10 to 50 μm. The thickness of the portions in conductive material is then greater, for example by 10 to 50 μm, than the thicknesses of the said insulating portion(s) of the second layer. The artificial retina of this embodiment is more efficient through the increased contact surface between the portions in conductive material and the neurons, and hence the increased quantity of charge that is able to be transmitted.

In general, the widths and lengths of the portions in conductive material are independent of each other and between entre 10 μm and 50 μm, particularly between 20 μm and 30 μm. For lengths or widths less than 10 μm, the resolution is generally insufficient and the current density is generally too strong, which increases the risks of damage to the neurons in contact with the retina. For an artificial retina of given surface area, the greater the lengths and/or widths of the portions in conductive material the fewer the number of portions of conductive material (and hence the fewer the number of pixels as explained below) and the more difficult it becomes for the artificial retina to reconstitute images. This is why the widths and lengths of the portions in conductive material are generally less than 50 μm. In general, the surfaces of the portions in conductive material are smaller than those of the portions in photovoltaic material.

The insulating material of the second layer is an insulating material compatible with the portions in conductive material and the first layer (portions in photovoltaic material and insulating portion of the first layer), notably allowing interface tensions to be minimized. This insulating material may in particular be insulating diamond or an insulating polymer. In general, the insulating material of the first and second layers is the same, which simplifies the preparation of the artificial retina.

In one embodiment, the conductive material is a metal, gold in particular, and the insulating material of the first and second layer is an insulating polymer. In another embodiment, the conductive material is a conductive diamond and the insulating material of the first and second layer is an insulating diamond.

If the second layer comprises more than one portion in insulating material, the lengths and widths of the portions in insulating material of the second layer are independently of each other generally between 1 µm and 50 µm, in particular between 5 µm and 20 µm.

The portions in insulating material of the first and second layers allow pixelation of the artificial retina. So that the artificial retina enables the individual in whom it is implanted to distinguish between shapes, recognize a face, read a letter, it is necessary that the retina should be structured so that it comprises several pixels.

This pixelation is obtained by means of the structure of the first and second layers. More specifically, each sub-assembly [substrate/portion in photovoltaic material/portion in conductive material] forms a pixel. The artificial retina comprises as many pixels as sub-assemblies [substrate/portion in photovoltaic material/portion in conductive material]. Each pixel must be electrically insulated from the other pixels, this insulation being ensured by the portions in insulating material. Therefore when only some areas of the artificial retina receive light, only some of the above-mentioned sub-assemblies (some pixels) convert the light to an electric signal transmitted locally to the retinal neurons in contact with these sub-assemblies, which allows image reconstitution.

The more the number of pixels in the artificial retina, the more shapes can be easily distinguished by the individual in whom the retina is implanted. Typically, the artificial retina comprises between 600 and 10 000 portions in conductive material, in particular from 1000 to 6000.

The first layer is a discontinuous layer comprising in its plane at least one portion in insulating material and portions in photovoltaic material. The second layer is a discontinuous layer comprising in its plane at least one portion in insulating material and portions in conductive material. In general, these layers only comprise one continuous portion of insulating material in which the portions in photovoltaic material (for the first layer) or conductive material (for the second layer) are dispersed. In another embodiment the first and/or second layers comprise several portions in insulating material separated from each other by the portions in photovoltaic material (for the first layer) or conductive material (for the second layer).

The portions in photovoltaic material and the portions in conductive material of the artificial retina are typically superimposed over each other i.e. when observing a vertical section of the artificial retina, one portion in conductive material is arranged above one portion in photovoltaic material (and not above a portion in insulating material of the first layer), as illustrated in FIG. 3. Each portion in photovoltaic material associated with a portion in conductive material forms a pixel with the substrate. Typically, the retina comprises as many portions in conductive material as portions in photovoltaic material. An artificial retina comprising a given number of pixels therefore comprises this same number of portions in photovoltaic material and this same number of portions in conductive material.

In general, the portion in conductive material has a smaller surface area than the underlying portion of photovoltaic material, so as to concentrate the emitted charges towards a single neuron or a small group of neurons.

FIG. 3 illustrates this embodiment for the case in which an artificial retina comprising a substrate (not illustrated), a first layer comprising at least one insulating material portion in insulating polymer and photovoltaic material portions in titanium dioxide (formed by layer-by-layer depositing of titanium dioxide and polyimide) and a second layer comprising portions in conductive material in gold separated by at least one insulating material portion in insulating polymer. Pixels formed of a localized surface of $TiO_2$, for example areas of 200 µm×200 µm, and of a localized gold surface, for example 10 µm×10 µm, are illustrated. Each pixel is insulated from the other pixels by an insulating polymer. Two pixels are illustrated in FIG. 3.

In one embodiment, the artificial retina further comprises a third layer arranged on the second layer and comprising a material promoting adhesion with the cells. For example, the retina may comprise a layer of poly-lysine, of elements of the extracellular matrix (laminins, collagens, fibronectin, vitronectin . . . ), or of Cell-Tak™ (polyphenol proteins produced by the mussel *Mytilus edulis*, distributed by BD Biosciences). However, this third layer is not compulsory since the retina normally sets up stable contact with the tissues on contact.

In one embodiment, the artificial retina further comprises a layer formed of a conductive material arranged between the substrate and the first layer.

This layer is preferably in Transparent Conductive Oxide (TCO) for example in fluorine-doped tin oxide (FTO) or indium-doped tin oxide (ITO).

According to a second aspect, the invention concerns a method for preparing the above-mentioned artificial retina comprising the steps of:

a) depositing a titanium-based semiconductor on a substrate to form a layer in photovoltaic material;

b) depositing a layer in conductive material on the layer in photovoltaic material obtained at step a) to form a layer in conductive material;

c) inserting at least one portion in insulating material in the layer in conductive material and in the layer in photovoltaic material to form the first and second layer.

At step a), the depositing of the titanium-based semiconductor is typically a layer-by-layer deposit.

The technique of layer-by-layer deposit allows a layer in photovoltaic material to be obtained from which the portions in photovoltaic material of the first layer of the artificial retina will be formed. The layer in photovoltaic material is the layer from which the first layer is formed comprising portions in photovoltaic material separated by at least one portion in insulating material. The layer in photovoltaic material therefore comprises the above-mentioned photovoltaic materials.

Layer-by-layer deposit is a technique for preparing thin layers, formed by alternate depositing of layers of material of opposite charge (assembly by electrostatic interactions) with rinsing steps between each depositing of a layer A layer is prepared from a solution comprising the titanium-based semiconductor or a precursor of the said semiconductor. A precursor is a chemical compound which, after layer-by-layer deposit and/or after chemical reaction, is converted to a titanium-based semiconductor. For example, titanium alkoxides such as titanium tetra-isopropoxide (TTIP) can be used for layer-by-layer depositing. The solution is generally an aqueous solution. The pH of the solution is adapted in relation to the isoelectric point of the titanium-based semiconductor to adjust the charge of the semiconductor. The isoelectric point is the pH at which the titanium-based semiconductor has a globally neutral charge. If the solution has a pH lower than the isoelectric point of the titanium-based semiconductor, its global charge will be positive and it will therefore form a layer with positive charge on the substrate. Conversely, if the solution has a pH higher than the isoelectric point of the titanium-based semiconductor, its global charge will be negative and it will therefore form a layer with negative charge on the substrate. Each titanium-based semiconductor has its own isoelectric point. Each crystalline form of titanium dioxide has its own isoelectric point.

Next, a layer with opposite charge is formed from a solution comprising a compound of opposite charge to the charge of the titanium-based semiconductor (or the precursor thereof).

Depending on experimental conditions and the type of titanium-based semiconductor, the layer comprising the titanium-based semiconductor may from the negative layer or the positive layer. In one embodiment, the layers of positive or negative charge are both formed from a titanium-based semiconductor (of opposite global charges).

In the embodiment in which the titanium-based semiconductor only forms one layer (either the positive charge layer of the negative charge layer), the compound(s) which form the intermediate layers between the layers of titanium-based semiconductor are biocompatible.

The positive layers are prepared from a solution comprising a salt, for example a solution of diallyldimethylammonium halide (depositing of the diallyldimethylammonium cation), or a compound protonated under the pH conditions used for deposit e.g. a polyethyleneiminium halide (depositing of the polyethyleneiminium cation). The chlorides, bromides and iodides are the preferred halides. Other salts can be used to form the positive layers (or negative layers if the titanium-based semiconductor forms the positive charge layer), for example those mentioned by G. Decher, J. B. Schlenoff in <<Multilayer thin films sequential assembly of nanocomposite materials>>, Wiley-VCH Eds, Weinheim, Germany, 2003, 524 pages.

The different layers of same charge in the layer of photovoltaic material may each comprise compounds of different type. For example it is possible to form a first layer with positive charge in polyethyleneiminium, then a negative charge layer in titanium dioxide, then a positive charge layer in diallyldimethylammonium, followed by a negative charge layer in titanium dioxide.

In one embodiment, step a) comprises the following steps:
i) immersing a substrate in an aqueous solution of polyethyleneiminium halide or diallyldimethylammonium halide;
ii) rinsing the substrate obtained at step i) with water;
iii) immersing the substrate obtained at step ii) in an aqueous solution of polyethyleneiminium halide or diallyldimethylammonium halide;
iv) rinsing the substrate obtained at step iii) with water;
v) immersing the substrate obtained at iv) in a solution comprising a titanium-based semiconductor,
vi) rinsing the substrate obtained at step v) with water, wherein the sequence of steps iii), iv), v) and vi) can be repeated, by which the titanium-based semiconductor is deposited layer by layer.

The technique of layer-by-layer deposit is a simple, low-cost technique allowing the thickness of each layer to be controlled. In general, the layer in photovoltaic material is prepared by depositing 2 to 10, in particular 2 to 5 layers of titanium-based semiconductor on the substrate.

To conduct step a), methods other than layer-by-layer deposit can be envisaged to prepare the layer in photovoltaic material, for example by thin layer deposit of titanium-based semiconductor in particular by evaporation, cathode sputtering or by lithography.

Step b) is preferably performed by physical or chemical vapor deposit or by lithography. Physical vapor deposit is a technique which consists of vacuum depositing a thin layer on a substrate by condensing the constituent material of the layer in conductive material to vaporized form. Chemical vapor deposit is a technique which consists of exposing a substrate to one or more precursors in gas phase, which react and/or decompose on the surface of the substrate to generate the desired deposit. Step b) can also be carried out by impregnating a precursor salt of the conductive material, then converting this precursor salt to the conductive material.

The layer in conductive material is the layer from which the second layer is formed which comprises portions in conductive material separated by at least one portion in insulating material. The layer in conductive material therefore comprises the above-mentioned conductive materials.

The method for preparing the artificial retina further comprises a step c) consisting of inserting at least one portion of insulating material in the layer of photovoltaic material (obtained at step a)) and in the layer of conductive material (obtained at step b)).

Typically step c) comprises a micro-etching step which allows the removal of localized areas of photovoltaic material and conductive material using a physical process (for example using a laser or by applying UV light) or a chemical process so as to obtain an inverted pattern of the desired marking. Then at least one insulating material is inserted in these areas to form the portions in insulating material of the first and second layers.

The insulating material can be inserted by lithography.

In general, to simplify the method, the same insulating material is inserted in the layer of photovoltaic material and in the layer of conductive material, and the artificial retina obtained therefore comprises portions in insulating material of same type in the first and second layers.

FIGURES

FIG. 1 illustrates a cross-section of the retina. 1: Pigment epithelium—2: Rods—3: Cones—4: External limiting membrane—5: Müller cells—6: Horizontal cells—7: Bipolar cells—8: Amacrine cells—9: Ganglion cells—10: Nerve fiber layer—11:—Inner limiting membrane.

FIG. 2 gives a cross-section of an eye and the positioning of the artificial retina in sub-retinal mode. 1: Sclera—2: Cornea—3: Pupil—4: Lens—5: Iris—6: Ciliary body—7: Optical nerve—8:—Retina—9: Choroid—10: Light.

FIG. 3 gives a schematic of a vertical section of an artificial retina illustrating a pixelation technique obtained by micro-etching, for an artificial retina comprising on a substrate (not illustrated) a first layer comprising an insulating material portion in insulating polymer and portions of photovoltaic material in titanium dioxide (formed by layer-by-layer deposit of titanium dioxide and polyimide) and a second layer comprising an insulating material portion in insulating polymer and portions in conductive material in gold. Two pixels each comprising a portion in $TiO_2$ photovoltaic material, for example over an area 200 μm×200 μm, and a portion in gold conductive material for example of given surface area 10 μm×10 μm are illustrated, each pixel being insulated from the other pixels by an insulating polymer FIG. 4 illustrates the currents recorded on PC12 cells cultured on a retina comprising 5 layers of titanium dioxide nanotubes, deposited by layer-by-layer technique, and gold in response to light flashes of 50 to 300 ms in blue light (100 W Xenon lamp with band-pass filter of 450-490 nm) (Example 2).

Figure 9:
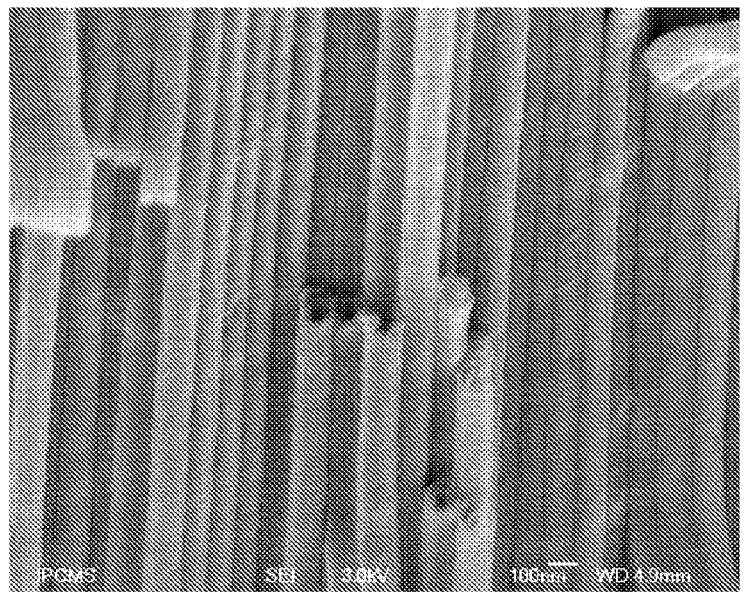
Figure 10:
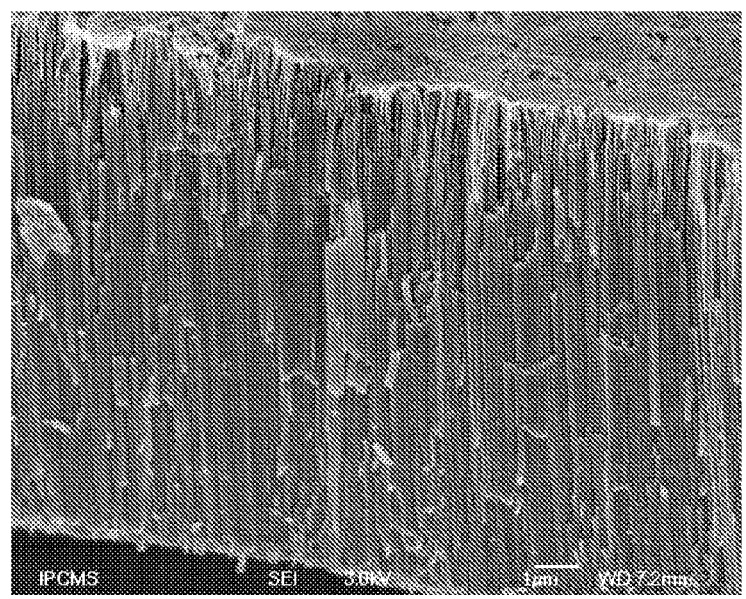

FIGS. 9 and 10 show the images obtained under microscopy (scanning electron microscope JEOL-JSM-6700F) for portions in photovoltaic material in TiO$_2$ in the form of nanotubes aligned relative to one another on a titanium substrate and synthesized with the following parameters: ethylene glycol electrolyte with 2% water by volume and 0.3 NH$_4$F by weight. Anodizing was performed with a voltage of 45 V for 2 hours. The images were obtained after heat treatment of the samples in a flow of air at 450° C. for 6 h (Example 4a).

Figure 11:
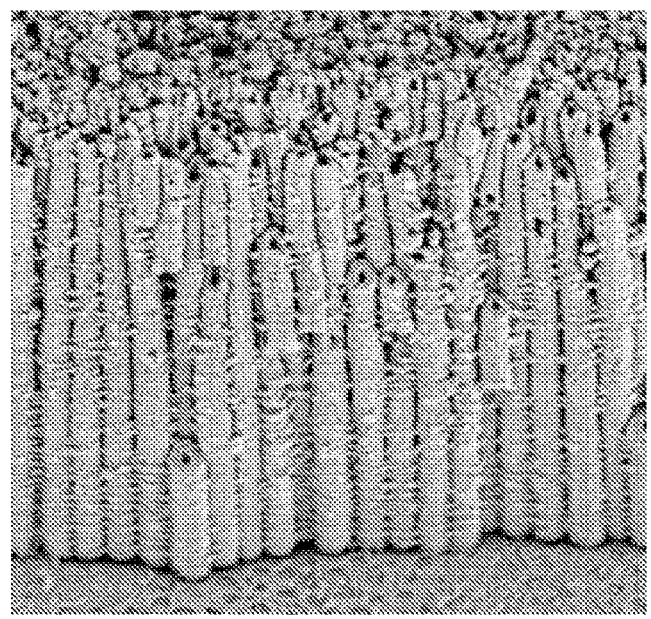

FIG. 11 shows an image obtained under microscopy (scanning electron microscope JEOL-JSM-6700F) for a portion in photovoltaic material in TiO$_2$ in the form of nanotubes aligned relative to one another on a silicon substrate (111) and synthesized following the protocol of Example 4b.

Figure 12:
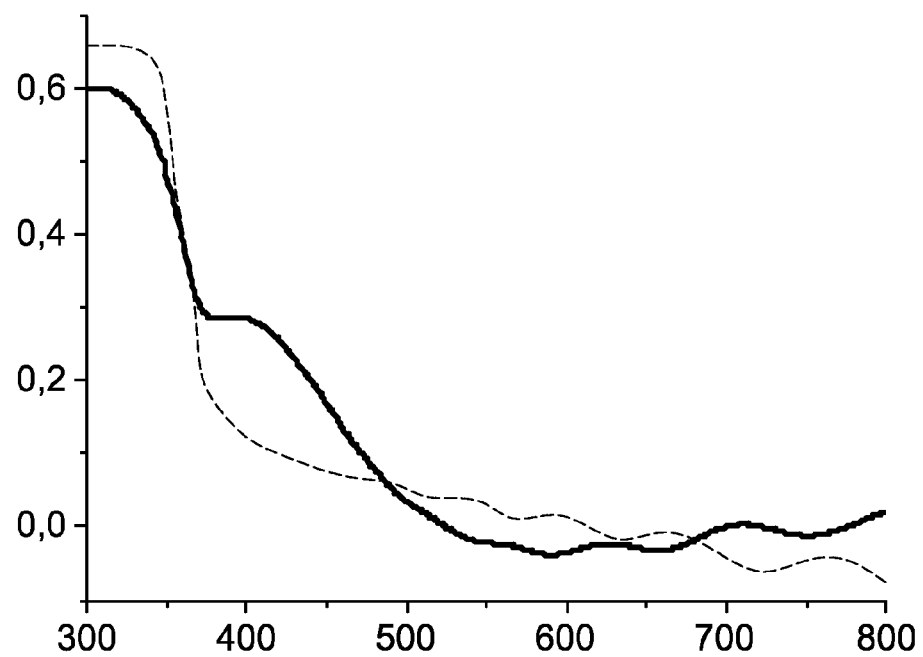

FIG. 12 gives the UV-visible spectra (absorbance in a.u. as a function of wavelength in nm) of the photovoltaic materials in Examples 4a) (dotted line) and 5 (solid line) (obtained with a UV-visible spectrometer CARY 100 SCAN by Varian, equipped with an integrating sphere: Labsphere DRA-CA-301).

Figure 13:
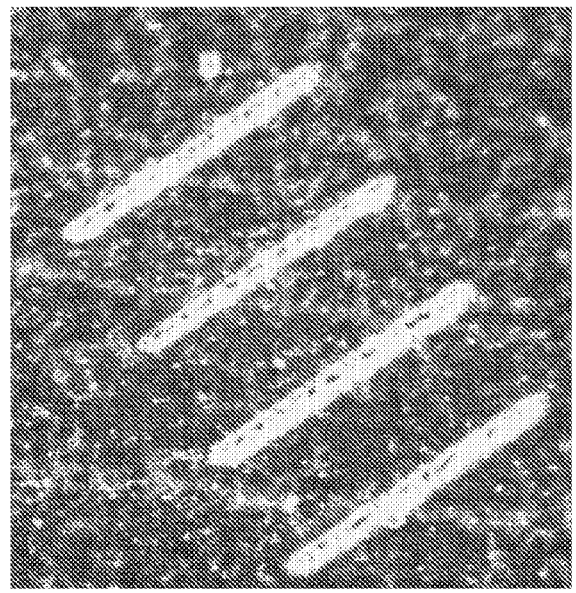

FIG. 13 shows a microscope image obtained under low-angle lighting (lens 40×) of the material in Example 6 obtained after laser machining.

Figure 14:
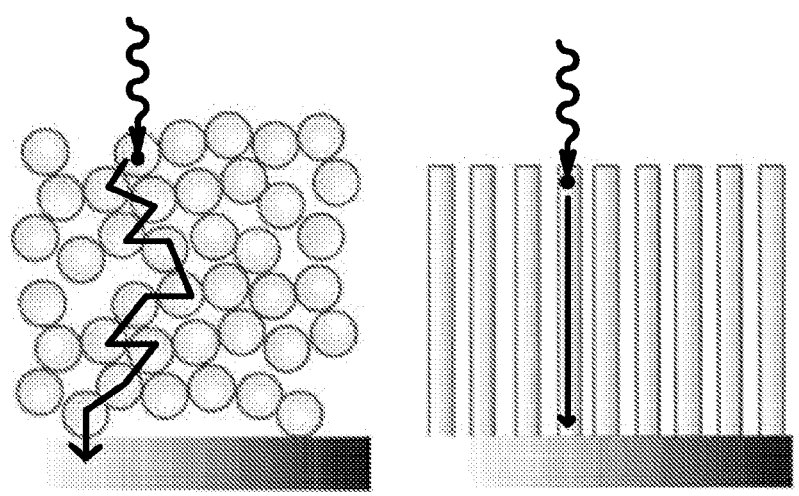

FIG. 14 schematically illustrates the pathway followed by the photogenerated electrons to pass through a retina comprising portions in photovoltaic material in the form of particles or entangled nanotubes (on the left) or in the form of nanotubes aligned relative to one another (on the right).

EXAMPLES

Examples 1 to 6 concern the preparation and use of a pixel of an artificial retina according to the invention. The exemplified artificial retinas do not contain a portion in insulating material. These examples show that a titanium-based semiconductor can be used as layer of photovoltaic material in an artificial retina.

Example 1

Retinas Comprising Titanium Dioxide and Gold

Example 1a

From Nanotubes of TiO$_2$

The nanotubes were synthesized by hydrothermal treatment at 150° C. for 72 hours of 700 mL of a 10 mol/L aqueous solution of sodium hydroxide comprising 7 g of TiO$_2$ (Degussa® P-25). The white precipitate obtained was then held in a vacuum in a desiccator at 500° C. for 18 hours. The nanotubes obtained were made oxygen-deficient by treatment in a flow of hydrogen for 2 hours at 350° C., this temperature having been reached by a rise in temperature of 5° C. per minute. With this treatment, the nanotubes can be activated by part of the visible sun spectrum.

The nanotubes were then dispersed in an ethanol/distilled water solution (50:50 by volume) having a pH adjusted to 9 under agitation for one hour to obtain a solution of dispersed nanotubes.

After pre-treating a silicon wafer by cleaning with a hydrochloric acid solution at pH 3, then with acetone and finally with ethanol under orbital agitation (10 minutes at 100 rpm for each cleaning) and drying the wafer for 5 minutes in a flow of hot air, layer-by-layer depositing (LbL) was conducted as follows:

1) This wafer was immersed in 50 mL of an aqueous 8 g/L solution of polyethyleneimine for 10 minutes and then rinsed by immersion in 50 mL of distilled water for 10 minutes.

2) The wafer was then immersed in 50 mL of an aqueous solution of 2 weight diallyldimethylammonium chloride for 10 minutes then rinsed by immersion in 50 mL of distilled water for 10 minutes.

3) The wafer was next immersed in 50 mL of the dispersed nanotube solution for 10 minutes then rinsed by immersion in 50 mL of distilled water for 10 minutes.

Steps 2) and 3) can be repeated to obtain multiple layers. In the example, these steps were repeated to obtain 5 and 10 layers of TiO$_2$ nanotubes on the silicon wafer.

After layer-by-layer deposit, the substrates were dried in air at ambient temperature, and a deposit of gold of nanometric thickness was then obtained by physical vapor deposition (PVD) for 2 minutes with an applied voltage of +22 mV at a pressure of 10$^{-6}$ bar.

Example 1b

From Commercial TiO$_2$

The dispersion of TiO$_2$ was obtained by placing in suspension 0.4 g of TiO$_2$ (P-25 Degussa-Evonik®) in 100 mL of an ethanol/distilled water solution (50:50 by volume) having a pH adjusted to 9 under agitation for one hour.

The subsequent steps of pre-treating a silicon wafer, layer-by-layer deposit of TiO$_2$ then depositing a layer of gold of nanometric thickness were conducted following the protocol of Example 1a), replacing the solution of dispersed nanotubes by the dispersion of TiO$_2$ for layer-by-layer depositing of TiO$_2$.

Example 2

Photoresponse of PC12 cells cultured on gold-coated TiO$_2$ Retina

Recordings were made using an electrophysiological technique called the patch clamp technique to record ion currents transiting through the cell membranes of PC12 cell line cells (derived from rat pheochromocytoma). These cells are routinely used as cell model in electrophysiology since their culture is easy and they can be differentiated into neurons by simply adding a nerve growth factor (NGF) to the culture medium (Greene & Tischler, P.N.A.S 1976, 73(7: 2424-8), cultured on glass slides coated with:

TiO$_2$ nanotubes (glass slides obtained after LbL deposit of 2, 5 or 10 layers of TiO$_2$ nanotubes, then coated with gold), or TiO$_2$ (P-25 Degussa-Evonik®) (glass slides obtained after LbL deposit of 2, 5 or 10 layers of TiO$_2$, then coated with gold), in a conventional cell culture medium (Dulbecco's medium: DMEM (Dulbecco/Vogt modified Eagle's minimal essential medium)) and 10% fetal calf serum). To increase cell adhesion, the glass slides were coated with poly-lysine (a polymer of the amino acid L-lysine). Under physiological pH conditions, poly-lysine forms a positively charged layer on the artificial retina which attracts the hydrophilic heads of the negatively charged membrane lipids. The <<whole cell>> configuration was used for direct measurement of all the ion currents passing through the cell membrane. The imposed potential was −70 mV.

Figure 1:
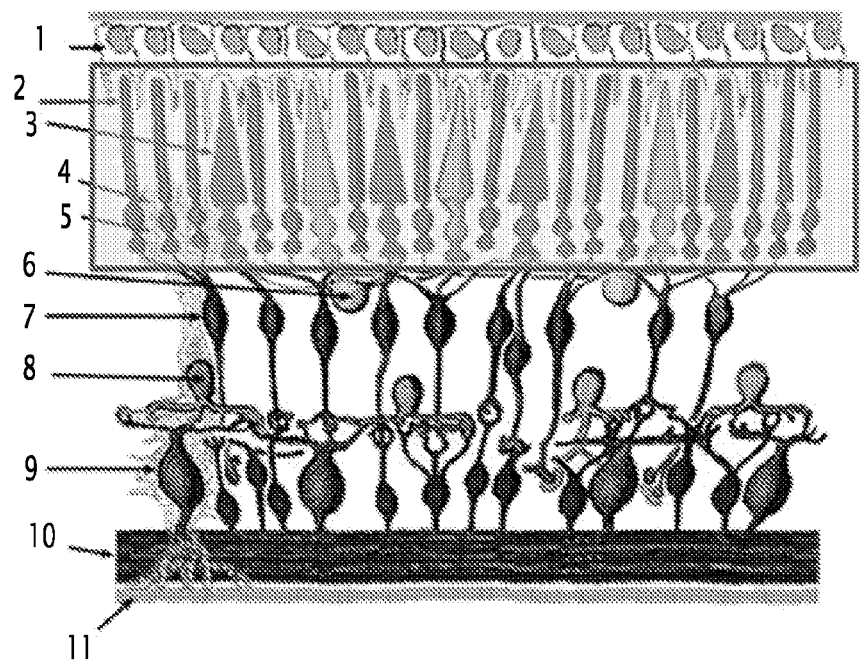
Figure 2:
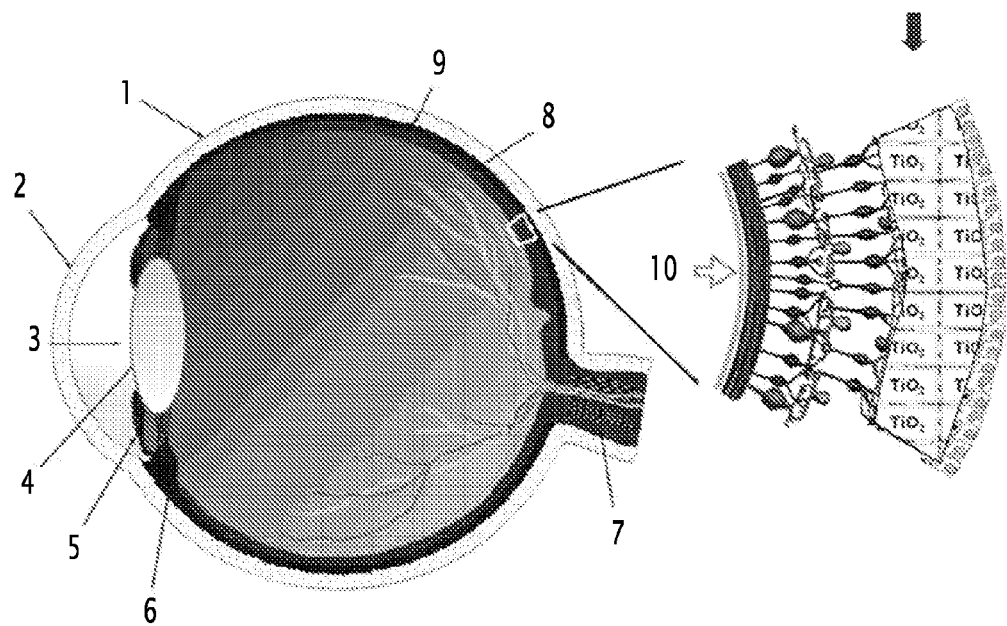
Figure 3:
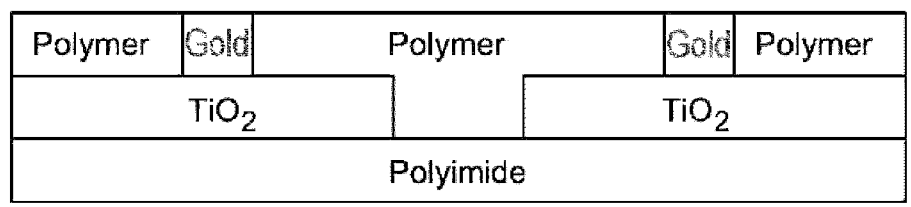
Figure 4:
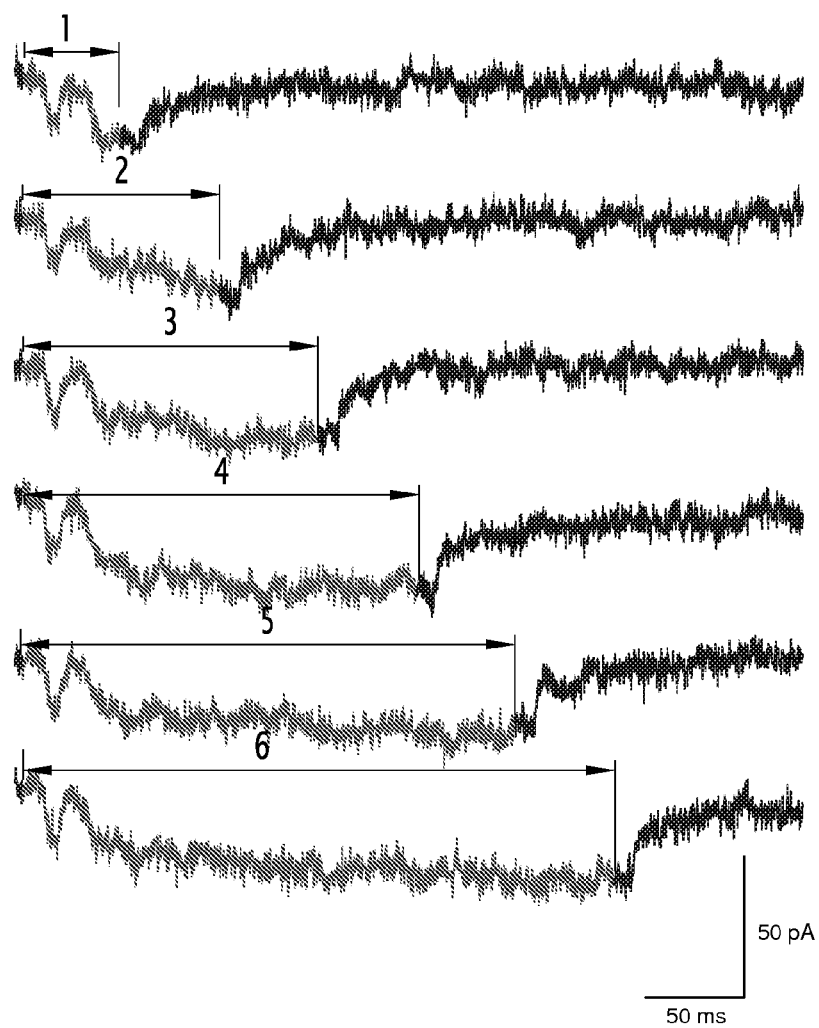
Figure 5:
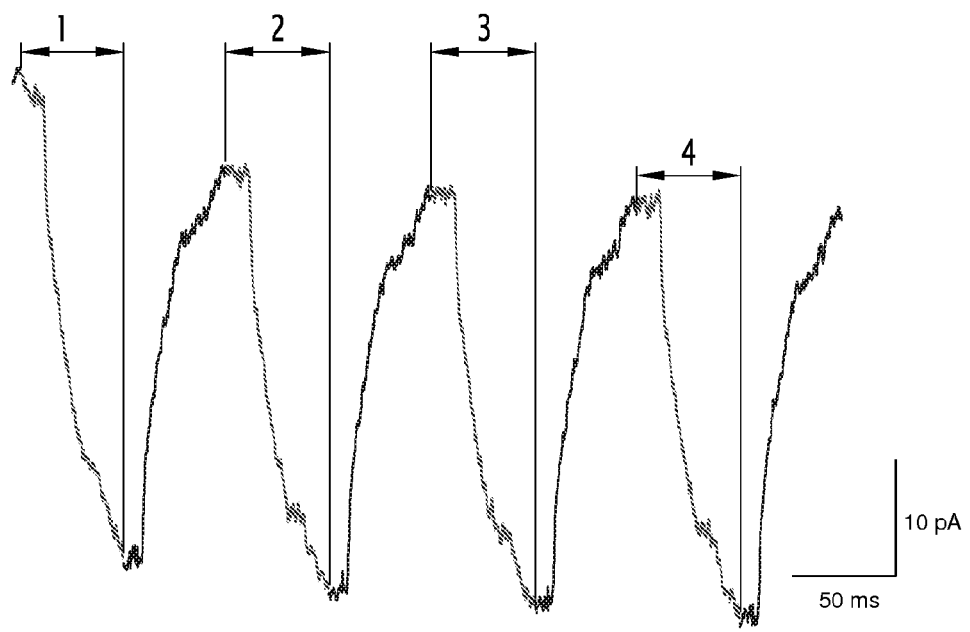
FIG. 5 shows the currents recorded on PC12 cells cultured on a retina comprising 2 layers of titanium dioxide (P-25 Degussa-Evonik®) deposited by layer-by-layer technique, and gold, in response to light flashes of 50 ms applied at a frequency of 10 Hz in green light (band-pass filter 530-560 nm) (Example 2).

FIGS. 4 and 5 illustrate the ion currents recorded on the PC12 cells cultured on two TiO$_2$/gold retinas, more precisely:

comprising 5 layers of titanium dioxide nanotubes deposited by layer-by-layer deposit and coated with gold in response to light flashes of 50 to 300 ms in blue light, comprising 2 layers of titanium dioxide (P-25 Degussa-Evonik®) deposited by layer-by-layer deposit and coated with gold in response to light flashes of 50 ms applied at a frequency of 10 Hz in green light.

The transmembrane current is the sum of the currents created by passing of the ions through the cell membrane. More specifically, a potential difference exists between the inside and outside of any living cell. The ions of the intra- and extracellular media move either side of the membrane, in accordance with the resultant of this potential gradient and the concentration gradient thereof via the ion channels. In a cell in good health, the inside of the cell is more negative than the outside. If the cell is maintained close to its equilibrium potential (−70 mV in the example), there is therefore very little current passing through the membrane. The net flow of the ions is then zero since the distribution of each ion species is close to its electrochemical equilibrium. On the other hand if the potential in contact with the cell is modified, in the example by passing a current through the TiO$_2$, the cell is no longer in equilibrium: the net flow of the ions through the membrane is no longer zero and a current is measured. This is negative i.e. there is a net entry of positive charges into the cell.

In the dark, the transmembrane current is identical to the one recorded for cells cultured on glass slides (in the absence of titanium dioxide) which are used as control.

On the other hand, an entering current is measured in response to a light flash for the cells cultured on TiO$_2$gold retinas, this not being the case for the cells cultured on glass slides. The duration of the response increases with the duration of the flash (FIG. 4). Flashes of 50 ms applied at a frequency of 10 Hz cause comparable currents (FIG. 5) without degradation of the state of the cell.

Figure 6:
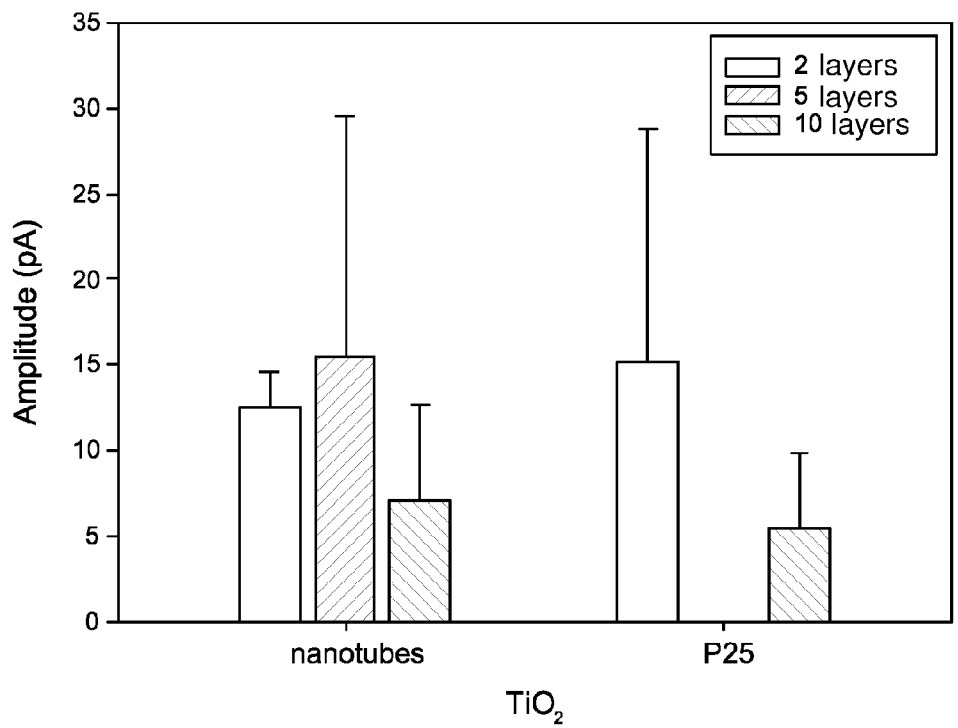
FIG. 6 illustrates the intensity of the currents (in pA) measured on PC12 cells cultured on a retina comprising 2, 5 or 10 layers of titanium dioxide whether or not in nanotube form deposited by layer-by-layer technique, and gold, in response to light flashes in blue light of 300 ms (450-490 nm, 320 mW/cm$^2$) (Example 2).

FIG. 6 illustrates the intensity of the currents (in pA) measured in response to light flashes in blue light of 300 ms on cultured PC12 cells in relation to the type of retina: retina comprising 2, 5 or 10 layers of titanium dioxide, whether or not in the form of nanotubes, and a layer of conductive material in gold. The intensities are similar whether the TiO$_2$ is or is not deposited in nanotube form. The measured intensities are higher for 2 or 5 layers of TiO$_2$ than for 10 layers.

Example 3

Biocompatibility of an Artificial Retina Comprising TiO$_2$ and Gold

Figure 7:
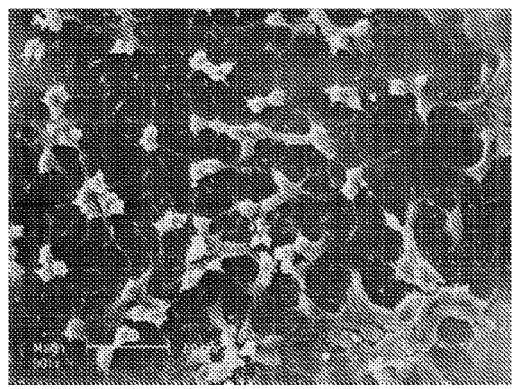
FIGS. 7 and 8 show the images observed under scanning electron microscopy of PC12 cells cultured on retinas comprising 5 layers of TiO$_2$ nanotubes and gold (Philips® XL 20 microscope).
Figure 8:
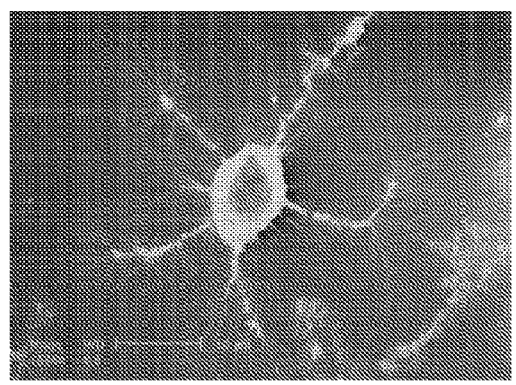

The biocompatibility of the titanium dioxide (whether or not coated with gold) was tested by comparing the growth rate of NG108-15 cells on artificial retinas prepared according to Examples 1a and 1b or on glass slides (controls) in both cases coated with poly-lysine to promote cell adhesion, in a DMEM/1% de fetal calf serum medium in order to slow the growth of the cells and enhance their neuronal phenotype. Whether on glass slides (controls) or on the different retinas comprising TiO$_2$, the cells seeded at $10^3$/cm$^2$ reached confluence after 12 days. The action potentials recorded for the cells on glass and on the retinas comprising TiO$_2$ are also very close. It was also observed that the PC12 cells growing on the TiO$_2$ form numerous extensions (FIGS. 7 and 8). To obtain the images under scanning microscopy in FIGS. 7 and 8, the cells were fixed in a buffer of sodium cacodylate containing 2.5% (weight/volume) of glutaraldehyde, then post-fixed for 1 h in the same buffer to which 1% osmic acid was added. The cells were then dehydrated, dried, metallized and observed under a Philips® XL 20 microscope.

All these data show that the artificial retinas comprising TiO$_2$ have good biocompatibility, meaning that they are advantageous for implanting.

Example 4

Retina Comprising a Photovoltaic Material in TiO$_2$ in the Form of Nanotubes Aligned Relative to One Another Example 4a Substrate in Titanium Before the experiment, titanium metal foil was cleaned by chemical scaling in aqua regia (HNO$_3$/HCl mixture: 3:1 by volume). It was then cleaned by ultrasound in successive baths of acetone, ethanol and ultrapure water (10 minutes in each solvent).

The foil thus obtained was placed in position in the electrochemical cell and the counter-electrode was also placed in position. The distance between the two electrodes was between 1 and 5 cm. The electrolyte used was ethylene glycol to which water and NH$_4$F (ammonium fluoride) were added in different proportions: water contents of between 0 and 20% by volume and contents of NH$_4$F of between 0.1 and 5 weight % were used. Under the tested conditions, the optimal synthesis parameters were water contents of between 1 and 2 volume % and 0.2 and 0.5 weight % of NH$_4$F. Under the tested conditions, the potential to be applied between the two electrodes was preferably between 20 and 100 V, in particular between 40 and 60 V, for efficient synthesis of the nanotubes. The length of synthesis may be between 10 minutes and 100 hours. The short times (between 15 minutes and 2 hours) allowed the formation of nanotubes well aligned relative to one another.

The films of TiO$_2$ nanotubes supported on titanium thus obtained were rinsed in ultrapure water to remove any remaining electrolyte.

Heat treatment was then performed for a time of 1 to 12 h under a flow of air at a temperature of between 400 and 600° C. A time of 2 h is sufficient for this heat treatment and a temperature of 450° C. is optimal. A typical example of the morphologies obtained is given in FIGS. 9 and 10. The nanotubes obtained with the above-described method have an outer diameter of the order of 100 nm. The inner diameter varies between 20 nm at the base of the tubes and 90 nm at the top. The length is strongly dependent on the duration of synthesis. For a synthesis time of 2 hours, a length of 15 μm is typically obtained.

Example 4b

Substrate in Silicon (111)

Depositing Titanium on a Silicon Substrate by Magnetron Sputtering

A target of metal titanium of high purity (99; 99%) was bombarded with ions derived from an argon plasma (plasma power 300 W, argon flow 20 sccm—current intensity 600 mA—temperature of 50° C.). The titanium atoms ejected from the target were deposited on the silicon substrate (111) placed facing the target. A layer of titanium 900 nm thick was deposited on the silicon.

Electrochemical Anodizing

Electrochemical anodizing of the silicon substrate on which the titanium was deposited was conducted in a glycerol electrolyte with 2% water by volume and 0.5 weight % of $NH_4F$. Optimal anodizing conditions were: 35 V for 4 hours at a temperature of 25° C. The film of aligned $TiO_2$ nanotubes obtained is illustrated in FIG. 11.

Example 5

Retina Comprising a Nitrogen-Doped Photovoltaic $TiO_2$ Material in the Form of Nanotubes Aligned Relative to One Another The preparation of the nanotubes by electrochemical anodizing was performed on titanium metal foil of 1×1 cm², in 100 mL of 1M electrolyte solution obtained as follows: 6.742 mL of concentrated $H_3PO_4$ (Fluka, 85%) were completed up to 100 mL with distilled water to obtain a 1M concentration before the addition of 1.167 mL of HF (i.e. 0.5 weight %). The electrolyte was stabilized at pH 5 with 4.88 g of NaOH. 3.03 g of urea $N_2COH_4$, i.e. a concentration of urea in the bath of 0.5 mol.$L^{-1}$ were then added as nitrogen source. Anodizing was performed with a potential of 20V for 4 hours.

Finally, heat treatment of 450° C. for 6 hours was conducted in a flow of nitrogen (100 mL/min, temperature ramp 2° C./min).

The spectra obtained by UV-visible spectroscopy for Example 4a) and for Example 5 are illustrated in FIG. 12. The presence of nitrogen in the nanotubes allows the absorption of part of visible radiation (wavelength>400 nm), which translates as the onset of a second absorption threshold at 530 nm.

Example 6

Micro-Etching of a Photovoltaic Material Allowing Pixelation of the Artificial Retina The method for preparing the artificial retina of the invention comprises a step (step c) consisting of inserting at least one portion of insulating material in the layer of photovoltaic material and in the layer of conductive material. This step comprises a micro-etching step to obtain an inverted pattern of the desired marking.

In this example micro-etching was conducted by laser removal of the material of Example 4a) in free air without the assistance of a gas in accordance with the following parameters:

| | |
|---|---|
| Focusing lens | LMU-15X-266 OFR |
| Laser | Nd:YAG QS 266 nm/10 ns HIPPO |
| Energy per pulse | <10 muW |
| Repeat rate | 50 kHz |
| Minimum exposure time | 1 s |

Lines 200 μm in length and 15 μm in width were traced at speeds of the order of 100 μm/s, as illustrated in FIG. 13. Repeat of the operation by performing orthogonal rotation allows the patterning of rectangles or squares, each rectangle/square obtained being one of the pixels of the artificial retina.

The invention claimed is:

1. An artificial retina comprising:
 (i) a substrate;
 (ii) a first layer placed onto the substrate comprising consisting of:
  (a) a plurality of portions consisting of photovoltaic material, wherein the photovoltaic material comprises a titanium dioxide semiconductor in the form of nanotubes, and
  (b) at least one portion consisting of insulating material;
   p1 wherein the plurality of portions consisting of photovoltaic material are separated by the at least one portion consisting of insulating material; and
 (iii) a second layer placed onto the first layer and comprising a plurality of conductive material portions separated by at least one insulating material portion.

2. The artificial retina according to claim 1, wherein the titanium dioxide semiconductor in the form of nanotubes is in the form of rutile, anatase, brookite, srilankite, $TiO_2$ α or $TiO_2$ β.

3. The artificial retina according to claim 1 wherein the nanotubes are aligned relative to one another.

4. The artificial retina according to claim 1, wherein the nanotubes are modified with a sensitizer.

5. The artificial retina according to claim 1, wherein the nanotubes are doped with nitrogen.

6. The artificial retina according to claim 1, wherein the plurality of conductive material portions are conductive diamond, titanium nitride, iridium oxide, a conductive polymer or a metal.

7. The artificial retina according to claim 1, wherein the insulating material of the first and/or second layer is an insulating diamond, a ceramic or an insulating polymer.

8. The artificial retina according to claim 1, wherein the photovoltaic material portions and the conductive material portions are superimposed over each other.

9. The artificial retina according to claim 1, wherein surfaces of the conductive material portions are smaller than surfaces of the photovoltaic material portions.

10. The artificial retina according to claim 1, wherein a thickness of the conductive material portions is greater than a thickness of the insulating portion of the second layer.

11. A method for preparing an artificial retina according to claim 1, comprising the steps of:
 a) depositing a titanium dioxide semiconductor in the form of nanotubes on a substrate to form a layer of photovoltaic material;
 b) depositing a layer of conductive material on the layer of photovoltaic material obtained at step a) to form a layer of conductive material;
 c) inserting at least one portion of an insulating material in the layer of conductive material and at least one portion of an insulating material in the layer of photovoltaic material to form the first and second layer.

12. The method according to claim 11, wherein step a) is performed using layer-by-layer deposit.

13. The method according to claim 11, wherein step b) is conducted by physical vapor deposition or chemical vapor deposition or by lithography.

14. The method according to claim 11, wherein step c) comprises a micro-etching or lithography step.

15. The artificial retina of claim 6, wherein the metal is gold or platinum.

* * * * *

UNITED STATES PATENT AND TRADEMARK OFFICE
CERTIFICATE OF CORRECTION

PATENT NO.         : 9,125,734 B2
APPLICATION NO.    : 13/514587
DATED              : September 8, 2015
INVENTOR(S)        : Nicolas Keller Page 1 of 1

It is certified that error appears in the above-identified patent and that said Letters Patent is hereby corrected as shown below:

Claims

In column 18 at line 17, In Claim 1, change "substrate comprising" to --substrate--.

In column 18 at line 24, In Claim 1, change "p1 wherein" to --wherein--.

Signed and Sealed this
Thirty-first Day of May, 2016

Michelle K. Lee
*Director of the United States Patent and Trademark Office*